United States Patent
Koch et al.

(10) Patent No.: US 10,427,739 B2
(45) Date of Patent: Oct. 1, 2019

(54) METHOD FOR AVOIDING EDGE CRACKS

(71) Applicant: GM GLOBAL TECHNOLOGY OPERATIONS LLC, Detroit, MI (US)

(72) Inventors: Niels Koch, Ruesselsheim (DE); Hauke Roth, Ruesselsheim (DE)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 244 days.

(21) Appl. No.: 15/454,996

(22) Filed: Mar. 9, 2017

(65) Prior Publication Data
US 2017/0259861 A1 Sep. 14, 2017

(30) Foreign Application Priority Data
Mar. 9, 2016 (DE) .................. 10 2016 002 889

(51) Int. Cl.
*G01M 5/00* (2006.01)
*B62D 65/02* (2006.01)
*G01N 3/08* (2006.01)

(52) U.S. Cl.
CPC ......... *B62D 65/028* (2013.01); *G01M 5/0033* (2013.01); *G01N 3/08* (2013.01); *G01N 2203/0062* (2013.01); *G01N 2203/0064* (2013.01)

(58) Field of Classification Search
CPC ........ B21D 28/16; B21D 28/00; B21D 35/00; B21D 35/001; Y10T 29/18; Y10T 29/49622; Y10T 29/49616
See application file for complete search history.

(56) References Cited

U.S. PATENT DOCUMENTS

| | | | |
|---|---|---|---|
| 2006/0137779 A1* | 6/2006 | Brodt | B21D 35/00 148/567 |
| 2011/0167608 A1* | 7/2011 | Niessen | B62D 65/028 29/428 |
| 2015/0082855 A1* | 3/2015 | Fujii | G06F 17/5018 72/379.2 |

FOREIGN PATENT DOCUMENTS

| | | |
|---|---|---|
| CN | 104215505 A | 12/2014 |
| CN | 204165807 U | 2/2015 |
| DE | 236995 A1 | 6/1986 |
| DE | 4127116 A1 | 2/1993 |
| DE | 10123302 A1 | 12/2002 |
| DE | 102007023605 A | 11/2007 |

(Continued)

OTHER PUBLICATIONS

German Patent Office, German Search Report for German Patent Application No. 10 2016 002 889.0 dated Dec. 9, 2016.

*Primary Examiner* — Jason L Vaughan
*Assistant Examiner* — Amanda Kreiling
(74) *Attorney, Agent, or Firm* — Lorenz & Kopf, LLP

(57) ABSTRACT

The present disclosure involves a method for determining the critical local expansion of a component with an eye toward the appearance of edge cracks based on an expansion of the component in the shaping process. Given a local expansion of the component at the edges that is smaller than the critical local expansion, no edge cracks arise that are larger than 1 μm. In particular, at least one expansion test is performed with at least one test component, and a critical overall expansion is determined with the at least one expansion test. The local maximum expansion of the test component is determined that the test component exhibits at the time of the critical overall expansion of the test component, and the local maximum expansion is the critical local expansion.

13 Claims, 3 Drawing Sheets

(56) References Cited

FOREIGN PATENT DOCUMENTS

| DE | 102009049155 A1 | 4/2011 |
|---|---|---|
| DE | 102012014258 A1 | 1/2014 |
| EP | 1785940 B1 | 1/2013 |

* cited by examiner

METHOD FOR AVOIDING EDGE CRACKS

CROSS-REFERENCE TO RELATED APPLICATION

This application claims priority to German Patent Application No. DE102016002889.0, filed Mar. 9, 2016, which is incorporated herein by reference in its entirety.

TECHNICAL FIELD

The present disclosure pertains to a method for determining the critical expansion of a component and a method for manufacturing a motor vehicle.

BACKGROUND

During the manufacture of motor vehicles, a component is separated from a blank component in a separation procedure, and the components are assembled into a body, in particular through welding and/or adhesive bonding. The blank component is generally a metal sheet unwound from a roll. The components are fabricated or separated out of the blank component in a separation process by punching. After the components have been fabricated, i.e., punched out of the blank component, the component is formed, thereby giving the component its final shape. For example, forming takes place by bending or deep drawing.

The forming process is accompanied by expansion, and cracks arise at the edges of the component, i.e., edge cracks come about if the local expansion in the area of the edges is greater than a critical local expansion. The critical local expansion is the expansion which, when exceeded, gives rise to edge cracks of a specific size, e.g., edge cracks visible to the naked eye. The local expansion depends on the geometry of the component, i.e., on the geometry of the punching tools, and/or on the geometry of the shaping process, e.g., a radius of curvature of the component generated by bending, i.e., preferably on the geometry of the tools used in shaping. The local expansion depends on the component geometry prior to shaping, because the component geometry helps determine the local expansion in the shaping process, i.e., for example, the same geometry of shaping can result in varying local expansions at different positions of the component.

The punching tools for punching the various components out of the blank component are expensive to manufacture. For this reason, the components are first fabricated out of the blank component in a test run through laser cutting. Components made by laser cutting are used in a test run to shape the components and subsequently put together the components with varying geometries to yield the body. While manufacturing the components by punching them out of the blank component, the punching process causes micro-cracks to form on the edges and/or the edges to become brittle. For this reason, components fabricated by being punched out of the blank component already exhibit edge cracks at smaller local expansions than components made via laser cutting, i.e., the critical local expansion is smaller for components made by punching than for components made by laser cutting. When manufacturing a motor vehicle or body in a test or trial run with components fabricated by laser cutting from the blank component, no edge cracks can thus initially arise on the component that are larger than a specific value.

As final operations for manufacturing the body of the motor vehicle begin, the components are fabricated by punching them out of the blank component with punching tools. In this final and complete startup of the process for manufacturing the body for the motor vehicle, edge cracks can therefore arise on the edges after shaping that are larger than a specific value. Such edge cracks are unacceptable for the quality of the body, so that these edge cracks must be finished in a complex manner and/or the expensive punching tools must be changed out accordingly, so that shaping is performed with components having a different original geometry prior to shaping, so that the local expansion is smaller than the critical local expansion for components fabricated by punching them out of the blank component. This is especially disadvantageous, since finishing, for example by grinding the edges, after shaping results in high costs for manufacturing the body over the long run, and changing out the punching tools prior to startup is associated with high costs, because new, different punching tools produce high costs.

DE 10 2009 049 155 A1 discloses a device for manufacturing a test specimen out of a sheet metal material, wherein the test specimen to be fabricated exhibits at least one outer edge to be tested. The device encompasses a cutting tool, which can be used to generate at least one outer edge to be tested as a cutting edge with a defined cutting edge progression, and the device further encompasses at least one heater, which can be used to heat the sheet metal material in advance in a defined manner, at least in the area of such a cutting edge to be generated.

EP 1 785 940 B1 shows a computer-implemented method for quantitatively characterizing one or several geometric parameters of an edge crack in a part, which is subjected to a manufacturing operation. A window size is set for processing a selectable number of imaging data points that correspond to a starting segment of an edge in the part. The window is displaced for processing corresponding imaging data points that correspond to sequential segments of the edge. At least one of the segments exhibits an edge crack in the part; generating a line formed by several interconnected lines based on a line adjustment for each sequential segment of the edge; calculating a difference in pitch along the interconnected lines for each sequential segment of the edge. A first edge crack point is identified based on a change in a variable for the calculated difference in pitch. The first edge crack point points to a first curved bend in the edge crack. A radius of curvature is calculated to characterize the first curved bend and determine whether the calculated radius satisfies a specified minimal value.

SUMMARY

The present disclosure provides a method for determining the critical expansion of a component and a method for manufacturing a motor vehicle in which essentially no edge cracks, in particular edge cracks visible to the naked eye, come about on the edges while and after shaping the component for the body. In particular, the method determines the critical local expansion of a component with an eye toward the appearance of edge cracks based on an expansion of the component in the shaping process, so that, given a local expansion of the component at the edges that is smaller than the critical local expansion, no edge cracks arise that are larger than 1 µm. In accordance with the method, at least one expansion test is performed with at least one test component. A critical overall expansion is determined with the at least one expansion test and/or as a function of the values from the at least one expansion test. The local maximum expansion of the test component is determined for the test component that exhibits the specific, critical overall expansion, and the local maximum expansion is the critical local expansion and/or the local maximum expansion of the test component is determined that the test component exhibits at the time of the critical overall expansion of the test component, and the local maximum expansion is the critical local expansion.

The test component and component are fabricated out of the same blank component with the same separating method. The local maximum expansion is determined for the test component at the time of the critical overall expansion of the test component, and this local maximum expansion is the critical local expansion of the test component and also of the component. Determined by empirical tests, this correlation makes it possible to easily determine the critical local expansion at which, when this critical local expansion is exceeded, edge cracks arise that are larger than a specific value, for example 1 μm. As a consequence, the critical local expansion can be determined especially easily for the components. This makes it especially easy to avoid edge cracks in components in the shaping process by correspondingly tailoring the geometry of shaping and/or the geometry of the component, so that the local expansions at the edges are smaller than the critical local expansion determined with this method.

In particular, several test components are used to perform a respective expansion test, and/or no edge cracks larger than 1 μm, 5 μm, 10 μm, 30 μm, 50 μm, 100 μm, 300 μm, 500 μm, 1000 μm arise on the edges at the local expansion of the component that is smaller than the critical local expansion. The values determined in the expansion tests, for example the tensile force-expansion curve, are determined in particular as the average of the tensile force-expansion curves determined in the various expansion tests.

In another embodiment, the critical overall expansion is manually determined graphically from at least one tensile force-expansion curve of the at least one expansion test, or the critical overall expansion is numerically determined from values of the at least one expansion test. During the expansion test, the beginning of expansion is accompanied by a preferably continually rising increase in tension, while the tension decreases starting at a specific expansion. The critical overall expansion is here an expansion that is larger than the expansion that arises at the maximum value for tension. In a numerical determination of the critical overall expansion, for example, the critical overall expansion is determined as a function of the expansion at which the maximum tension arises. For example, the critical overall expansion is the expansion that corresponds to 110%, 120% or 140% of the overall expansion at the maximum tension. This also makes the critical overall expansion especially easy to numerically determine.

In a supplementary embodiment, the critical overall expansion is determined in several expansion tests from an average of the values for the expansion tests. The several expansion tests are best performed with identical test components.

In an additional variant, the critical overall expansion is determined in several expansion tests, in that the parameter for the difference in tensile forces between the at least two tensile force-expansion curves is determined for at least two expansion tests, and once a prescribed value for the parameter has been reached, the existing overall expansion is the critical overall expansion. The parameter can be expressed as an absolute value, for example as the difference between the tensile forces, or also as a percentage value relative to the tensile forces.

The local maximum expansion of the test component is preferably determined via finite element method (FEM). The local maximum expansion can thus be easily determined with the FEM. The geometry of the test component and also the direction of expansion are known, so that the local maximum expansion can be easily determined with the FEM.

In a variant, the local maximum expansion is determined via local expansion measurements on the test component. While performing the expansion test on the test component in a corresponding testing device, corresponding expansion measurements can be implemented on the test component, for example with expansion measuring strips, so that the local maximum expansion of the test component can thereby also be determined through measurement.

It is best that the test component includes the same material and same thickness prior to the expansion test as the component prior to shaping. This is necessary so that the critical local expansion of the test component be identical to the critical local expansion of the component for the body. In another embodiment, the test component and component are fabricated out of the same blank component.

In particular, the test component and component are fabricated out of the same blank component with the same separating method, in particular punching or laser cutting. The test component and component are made out of the same blank component, i.e., exhibit the same material and same thickness. Further, the material structure is identical at the edges owing to the same separating method used for fabrication out of the blank component. As a result, a test component fabricated by punching it out of a blank component can be used to determine the critical local expansion for components manufactured by punching them out of the blank component. This also holds true analogously for test components fabricated via laser cutting, so that the test components fabricated out of the blank components via laser cutting are used to determine the critical local expansion for components fabricated via laser cutting.

A method according to the present disclosure for manufacturing a motor vehicle includes: fabricating components by separating the components out of a blank component by a separating method; shaping the components; and assembling the components into a body of the motor vehicle. The geometry for shaping the components and/or the geometry for the components fabricated in the separating method is designed so that the local expansion at the edges of the components is smaller than the critical local expansion of the components relative to the appearance of edge cracks due to the expansion of the component while shaping the components, so that essentially no cracks larger than 1 μm are present on the edges of the components after shaping the components. After the components have been fabricated out of the blank component via the separating method, the components are at first generally flat in design. Shaping brings about a plastic deformation in the geometry of the components. For example, the components exhibit a corresponding curvature on the surface after shaping and/or exhibit a smaller thickness owing to an expansion.

Calculating methods, in particular FEM, can be used to determine the local expansion on the edges from the shaping geometry. The critical local expansion of the components starting at which edge cracks of a specific size arise is known. For this reason, the reshaping geometry, in particular the shape of the tools for shaping the components, is configured in such a way that the local expansions at the edges of the components are smaller than the critical local expansion of the components. As a result, no edge cracks larger than a specific value advantageously appear after shaping the components. As a consequence, before the final startup of a production line for manufacturing the body, the punching tools and/or the tools for shaping the components can be advantageously configured in such a way prior to fabricating the punching tools and/or prior to fabricating the tools for shaping the components that no edge cracks arise after the shaping process.

After the final startup of the production line, the punching tools and/or tools for shaping the components thus need not be changed out. As a consequence, the costs for manufacturing the body of the motor vehicle can be significantly reduced. The geometry for shaping the components determines the expansion, in particular the local expansion, of the components in the shaping process. In particular, the shaping geometry is the changing of shaping geometry, for example a specific radius of curvature for the component after shaping, because the component is flat prior to shaping, and/or the change in geometry in the shaping process and/or the change in shape in the shaping process. The shaping geometry also determines the position on the component in which shaping is implemented.

In another embodiment, the critical local expansion of the components is determined with respect to the appearance of edge cracks due to an expansion of the components in a method described in this patent application. In a supplemental variant, the critical local expansion is determined prior to shaping the components, and the geometry of shaping the components and/or the geometry of the components fabricated in the separating method are determined as a function of the critical local expansion, which is determined as described in this application, to ensure that the expansion in particular at the edges is smaller while shaping the components than the clinical local expansion determined as described in this patent application and/or that no cracks are present at the edges of the components after shaping that are larger than 5 µm, 10 µm, 30 µm, 50 µm, 100 µm, 300 µm, 500 µm, 1000 µm.

In another variant, the components are fabricated in a separating method that involves punching them out of the blank component, in particular a metal sheet unwound from a roll. In another embodiment, the components are assembled by welding and/or adhesive bonding. In an additional embodiment, shaping takes place through bending and/or deep drawing and/or shearing. In a supplemental embodiment, the components are fabricated by punching out of the blank component. In another embodiment, the components and at least one test component are made out of metal, in particular steel and/or aluminum.

In a supplemental variant, the at least one test component is fabricated out of the blank component via wire erosion. The test component is thus made with a cutting wire through wire erosion, wherein essentially the same structural changes arise during this separating method as in laser cutting. In order to determine the critical overall expansion of the at least one test specimen fabricated via laser cutting, the at least one test specimen can thus be fabricated with a sufficient accuracy through wire erosion instead of laser cutting.

A method according to the present disclosure for manufacturing a motor vehicle includes: fabricating components by punching the components out of a blank component; shaping the components; and assembling the components into a body of the motor vehicle. The critical local expansion for components fabricated through laser cutting is determined, the critical local expansion for components fabricated through punching is determined, and the difference in expansion between the critical local expansion for components fabricated through laser cutting and the critical local expansion for components fabricated through punching is determined. The geometry for shaping the components and/or the geometry of components fabricated through punching is such that the local expansion at the edges of the components is smaller than the local expansion of the components fabricated in a trial run with laser cutting minus the determined difference in expansion, so that after the components have been shaped, essentially no cracks larger than 1 µm are present on the edges of the components. In a trial run, the components are first fabricated by laser cutting from the blank component, and then shaped and assembled into the body, so that essentially no cracks larger than 1 µm are present at the edges of the components during the trial run. After the manufacturing process has been changed over from the trial run performed with components fabricated via laser cutting to the final and complete manufacturing process performed with components fabricated via punches, the local expansion at the edges while shaping in the final manufacturing process is smaller than the local expansion while shaping in the trial run minus the determined difference in expansion, so that no relevant cracks arise at the edges in the final manufacturing process. The components fabricated via laser cutting and punching are preferably made out the same blank component.

The present disclosure further encompasses a computer program with program code means, which are stored on a non-transitory computer-readable data carrier in order to implement a method described in this patent application when the computer program is executed on a computer or corresponding computing unit. Another constituent of the present disclosure is a computer program product with program code means, which are stored on a computer-readable data carrier in order to implement a method described in this patent application when the computer program is executed on a computer or corresponding computing unit.

BRIEF DESCRIPTION OF THE DRAWINGS

The present disclosure will hereinafter be described in conjunction with the following drawing figures, wherein like numerals denote like elements.

DETAILED DESCRIPTION

The following detailed description is merely exemplary in nature and is not intended to limit the present disclosure or the application and uses of the present disclosure. Furthermore, there is no intention to be bound by any theory presented in the preceding background of the present disclosure or the following detailed description.

Figure 1:
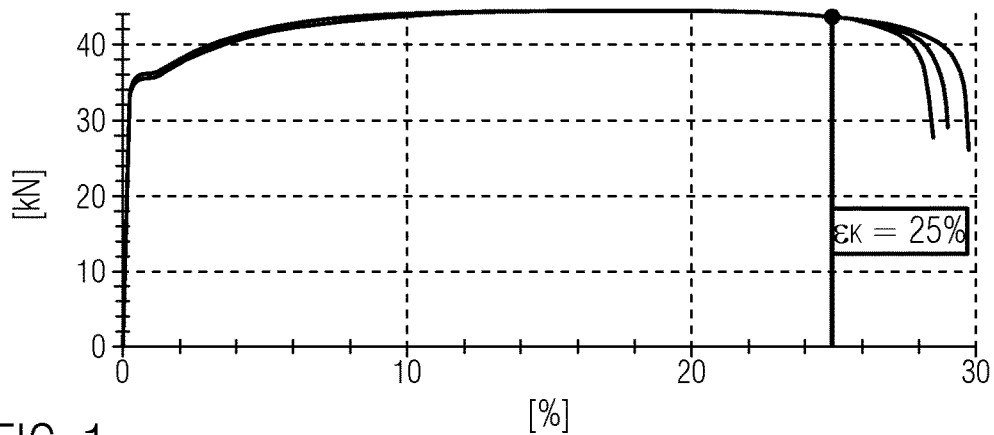
FIG. 1 is a tensile force-expansion curve with tensile force plotted on the abscissa and tension plotted on the ordinate for a test component fabricated via laser cutting.
Figure 2:
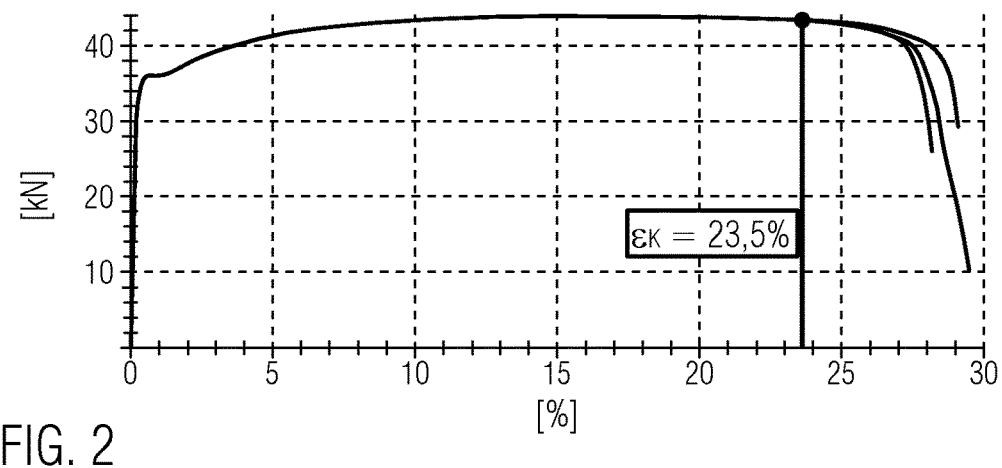
FIG. 2 is a tensile force-expansion curve with tensile force plotted on the abscissa and tension plotted on the ordinate for a test component fabricated via punching.

A motor vehicle 1 shown on FIG. 1 exhibits a body 2 made of steel. A drive engine 3, specifically an electric motor 4 and/or an internal combustion engine 5, drives the motor vehicle 1. The body 2 borders an interior space in which is located seats 6, specifically front seats 7 and rear seats 8, for accommodating passengers or persons.

The body 2 of the motor vehicle is assembled out of components 9 made of steel. The components 9 with varying geometries are joined together in a welding line via welding as the joining process. Before the components 9 are joined together, the components 9 are fabricated out of a blank component 19. The blank component 19 is a metal sheet, which is unwound from a roll 20. The components 9 with the varying geometries are fabricated out of the blank component 19 through punching with punching tools having a varying geometry. The components 9 here exhibit an outer edge 11 as one edge 10, and the components 9 can further also exhibit a borehole 14 and/or a recess 15. At the boreholes 14, an edge 12 here arises at the borehole 14, and at the recess 15, edges 13 arise at the recess 15.

After the components 9 have been punched out of the blank component 19, the components 9 as a rule have to be shaped, for example bent or deep drawn. The varying geometries and the varying positions for forming on the component 9 result in different local expansions on the component 9. The smaller a radius of curvature with which the initially flat component 9 is here bent, the greater the local expansion while shaping the component 9. Starting at a specific critical local expansion of the component 9 in the shaping process, edge cracks appear at the edges 10 starting at a specific size, e.g., 10 μm. Such edge cracks diminish the quality of the body 2, so that these edge cracks must be avoided starting at a specific size. The local expansions on the component 9 that arise while shaping can be calculated with the finite element method (FEM), for example, or by corresponding measurements. The geometry for shaping and/or the geometry of the components 9 after separated from the blank component 19 and prior to shaping is here prescribed by the structural requirements on the body 2, while these structural requirements can also be correspondingly adjusted and changed.

In a test or trial run for manufacturing the body 2 of the motor vehicle 1, the components 9 are fabricated out of the blank component 19 not by punching with a punching tool, but rather by laser cutting. This is done via laser cutting because punching tools are initially very expensive to manufacture, and when using laser cutting as the separation process, varying geometries for components 9 can be fabricated out of the blank component 19 only by reprogramming the laser cutting system. After the components 9 have been manufactured in this way in the test run, the components 9 are correspondingly shaped via corresponding tools for shaping, for example presses. However, structural changes arise at the edges 10 of the components 9 that are different during punching than during laser cutting. Punching is accompanied by micro-cracks along with embrittlement of the edges 10, so that the critical local expansion is resultantly smaller in components 9 made via punching than in components 9 made via laser cutting. In the test or trial run for manufacturing the body 2 of the motor vehicle 1, no edge cracks can thus arise initially on the edges 10 of the components 9 during the test or trial run performed with components 9 fabricated by laser cutting out of the blank component 19.

During the final and complete startup of the production line for manufacturing the body 2 of the motor vehicle, all components 9 are punched out of the blank component 19 by corresponding punching tools owing to the high number of components 9 to be fabricated. Three test components 6 are fabricated out of the blank component 19 via punching, and three additional test components 16 are fabricated via laser cutting. The three test components 16 made by laser cutting are sequentially subjected to an expansion test in a corresponding test device. FIG. 1 shows the three tensile force-expansion curves for these three test components 16. Expansion in % is plotted on the abscissa, and the tensile force kN is plotted on the ordinate. Given an expansion of roughly 15%, the maximum tensile force arises, after which a reduction in tensile force arises given a further expansion.

An operator uses this tensile force-expansion curve shown on FIG. 1 to manually determine a critical overall expansion $\varepsilon_k$, either visually or with numerical methods. The critical overall expansion $\varepsilon_k$ is here larger than the expansion with a maximum tensile force, and, for example, measures a specific percentage value of expansion with the maximum tensile force, and the critical expansion is larger than the expansion with the maximum tensile force. The critical overall expansion $\varepsilon_k$ is here encountered at a value for expansion at which the tensile force-expansion curves for the three test components 16 do not yet essentially move apart, i.e., the difference in tensile forces is small given a respectively identical overall expansion. The critical overall expansion $\varepsilon_k$ for the test components 16 fabricated via laser cutting measures 25%.

Figure 3:
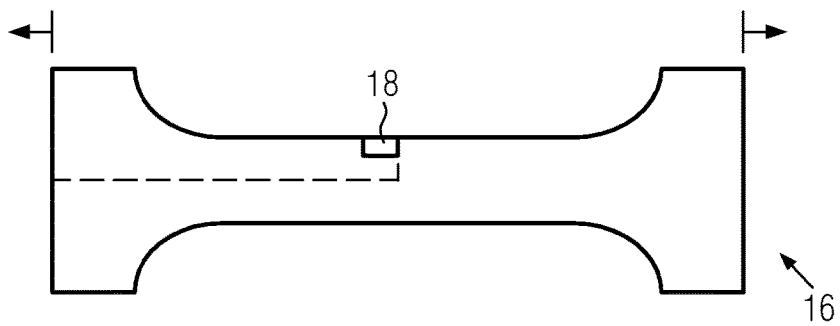
FIG. 3 is a top view of a test component.
Figure 4:
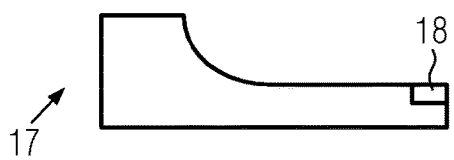
FIG. 4 is a top view of an imaginary part of the test component according to FIG. 3.
Figure 5:
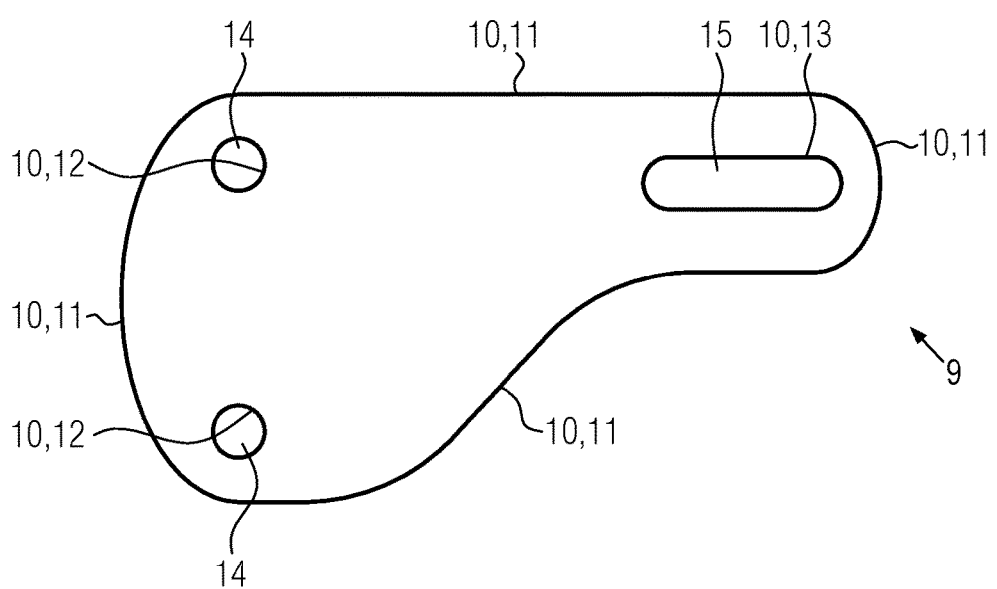
FIG. 5 is a top view of a component for manufacturing a body.
Figure 6:
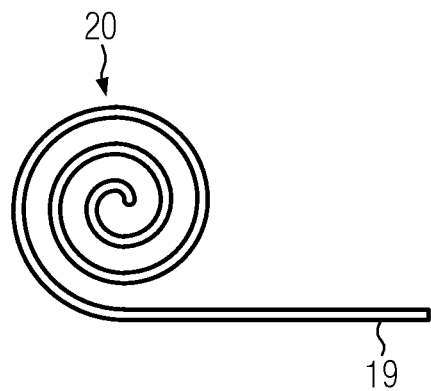
FIG. 6 is a side view of a blank component unwound from a roll.
Figure 7:
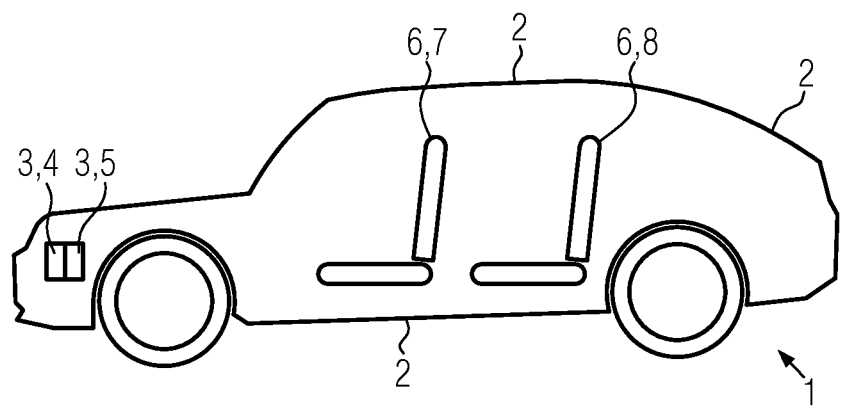
FIG. 7 is a side view of a motor vehicle.

In like manner, this expansion test is carried out with three test components 16 fabricated via punching out of the blank component 9. The critical overall expansion $\varepsilon_k$ for these three test components 16 fabricated via punching measures 23.5%. The expansion test is here performed as a tensile test, i.e., the test component 16 shown on FIG. 3 is exposed to a tensile force at the respective two end sections depicted on the left and right of FIG. 3, so that a tensile expansion of the test component 16 thereby arises. A local region 18 with a maximum expansion comes about in the middle of the test component 16 during the expansion test. The test component 16 exhibits two symmetrical axes that rest perpendicular one on the other, and a part of these two symmetrical axes is shown with dashed lines on FIG. 3. One fourth of the test component 16 as an imaginary part 17 of the test component 16, i.e., the left upper fourth on FIG. 3, which is imaginarily separated from the two symmetrical axes, is here subjected to a calculation process with the finite element method. This finite element method can be used to determine the expansion of the test component 16 at all local regions based on the symmetry of the arising local expansions, and to determine the local region 18 with the maximum expansion. The critical overall expansion $\varepsilon_k$ for the components 16 fabricated via punching is analogously determined, and measures 23.5%. The individual local expansions of the test component 16 at the time when the critical overall expansion is 23.5% can be determined with the finite element method, and the local region 18 with the maximum expansion can be determined from the latter. The critical local expansion of the test component 16, i.e., the local region 18 with the maximum expansion at the time when the critical overall expansion $\varepsilon_k$ for the test component 16, here measures 41%.

When manufacturing the components 9 by punching them out of the blank component 9 and then shaping the components 9, the geometry of the components 9 after punching, i.e., and thus the geometry of the punching tools and shaping geometry, i.e., for example also for the geometry of the tools for shaping, must be configured in such a way that the local expansions arising at the edges 10 of the components 9 in the shaping process are smaller than the critical local expansion of 41%. During final startup of the production line for the body 2 of the motor vehicle 1, the critical local expansion can be determined in advance so as to design the punching tools and/or tools for shaping the components 9 in such a way that the local expansions at the edges 10 of the components 9 are smaller than the critical local expansion of 41% in the shaping process, and hence that no edge cracks, for example those larger than 10 μm, advantageously arise on the edges 10 after the components 9 have been shaped.

Analogously, the critical local expansion can also be determined for the test components 16 fabricated through laser cutting from a blank component 19, and measures 51%. The critical local expansion for components 9 fabricated via laser cutting serves on the one hand as a comparative value for the critical local expansion for the components 9 fabricated via punching, and on the other for determining the difference in expansion.

Viewed as a whole, significant advantages are associated with the method according to the present disclosure for determining the critical local expansion and the method according to the present disclosure for manufacturing the motor vehicle. The critical local expansion of the components 9 starting at which edge cracks of a specific size arise can be easily determined with empirical methods, as described above. Because this critical local expansion starting at which relevant edge cracks arise is known, the geometry of the punching tools and/or the geometry of the tools for shaping the components 9 and/or the geometry of shaping can be designed in such a way prior to final startup of the process for manufacturing the body 2 of the motor vehicle 1 that the local expansions at the edges 10 of the components 9 are smaller than the critical local expansion in the shaping process. After final startup of the process for manufacturing the body 2 of the motor vehicle 1, no finishing of the edges 10 of the components 9 is thus required after shaping, in addition to which the punching tools and/or tools for shaping the components 9 also need not be changed out.

When determining the difference in expansion between the critical local expansion of components 9 fabricated via laser cutting and the critical local expansion of components 9 fabricated via punching, this determined difference in expansion can be used during conversion from the test run to final startup with the difference in expansion to indicate how much smaller the expansion in the shaping process during final startup must be than during the test run, so as to prevent any relevant cracks from arising during final startup. However, this presumes that no relevant cracks were encountered during the test run either. As a result, the costs for manufacturing the body 2 of the motor vehicle 1 can be reduced with little effort.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the present disclosure as set forth in the appended claims and their legal equivalents.

What is claimed is:

1. A method for manufacturing a motor vehicle comprising:
   separating a component out of a blank component by a separating method;
   shaping the component;
   assembling the component into a body of the motor vehicle;
   determining the critical local expansion of the component with respect to the appearance of edge cracks due to an expansion of the component in a method wherein:
     at least one expansion test is performed with at least one test component; and
     a critical overall expansion is determined with the at least one expansion test;
     wherein a local maximum expansion of the at least one test component is determined that the at least one test component exhibits at the time of the critical overall expansion of the at least one test component, and the local maximum expansion is the critical local expansion,
   wherein a geometry for shaping the component and a geometry for the component fabricated in the separating method is configured such that a local expansion at an edge of the component is less than the critical local expansion of the component relative to an appearance of edge cracks due to the expansion of the component while shaping the component such that no cracks larger than 1 μm are present on the edge of the component after shaping the component and the method further comprises determining the critical local expansion prior to shaping the component, and the geometry of shaping the component and the geometry of the component fabricated in the separating method are determined as a function of the critical local expansion determined to ensure that the expansion at the edge is smaller while shaping the component than the critical local expansion.

2. The method according to claim 1, further comprising performing a plurality of expansion test with a plurality of test components.

3. The method according to claim 2, further comprising determining the critical overall expansion in several expansion tests, wherein a parameter for the difference in tensile forces between at least two tensile force-expansion curves is determined for at least two expansion tests, and once a prescribed value for the parameter has been reached, the existing overall expansion is the critical overall expansion.

4. The method according to claim 1, further comprising graphically determining the critical overall expansion from at least one tensile force-expansion curve of the expansion test, wherein the critical overall expansion is numerically determined from values of the at least one expansion test.

5. The method according to claim 1, further comprising determining the local maximum expansion of the test component with finite element methods.

6. The method according to claim 1, further comprising determining the local maximum expansion via local expansion measurements on the test component.

7. The method according to claim 1, wherein the test component comprises the same material and same thickness prior to the expansion test as the component prior to shaping.

8. The method according to claim 7, further comprising fabricating the test component and component out of the same blank component.

9. The method according to claim 8, further comprising fabricating the test component and component with the same separating method.

10. The method according to claim 9, wherein the separating method is selected from the group consisting of punching and laser cutting.

11. The method according to claim 1, wherein separating a component comprises punching the component out of a metal sheet unwound from a roll.

12. The method according to claim 1, further comprising assembling the component by a joining process selected from the group consisting of a welding process, an adhesive bonding process or a combination thereof.

13. The method according to claim 1, further comprising shaping the component by a forming process selected from the group consisting of a bending process, a deep drawing process, a shearing process or a combination thereof.

* * * * *